(12) United States Patent
Salvatore (10) Patent No.: US 10,919,906 B2
(45) Date of Patent: Feb. 16, 2021

(54) CONFORMATIONALLY-CONSTRAINED BIOISOSTERES OF CAFFEIC ACID, AND SYNTHESIS AND THERAPEUTIC USES

(71) Applicant: Board of Supervisors of Louisiana State University and Agricultural and Mechanical College, Baton Rouge, LA (US)

(72) Inventor: Brian Salvatore, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 16/259,383

(22) Filed: Jan. 28, 2019

(65) Prior Publication Data

US 2019/0233429 A1    Aug. 1, 2019

Related U.S. Application Data

(60) Provisional application No. 62/622,805, filed on Jan. 26, 2018, provisional application No. 62/622,808, filed on Jan. 26, 2018, provisional application No. 62/622,811, filed on Jan. 26, 2018, provisional application No. 62/622,818, filed on Jan. 26, 2018, provisional application No. 62/622,820, filed on Jan. 26, 2018, provisional application No. 62/622,822, filed on Jan. 26, 2018.

(51) Int. Cl.
*C07D 493/04* (2006.01)
*C07D 405/04* (2006.01)
*C07D 311/04* (2006.01)
*A61P 35/00* (2006.01)

(52) U.S. Cl.
CPC ............ *C07D 493/04* (2013.01); *A61P 35/00* (2018.01); *C07D 311/04* (2013.01); *C07D 405/04* (2013.01)

(58) Field of Classification Search
CPC .. C07D 493/04; C07D 311/04; C07D 405/04; A61P 35/00
USPC ........................................................ 514/382
See application file for complete search history.

(56) References Cited

PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*

* cited by examiner

*Primary Examiner* — Kristin A Vajda
(74) *Attorney, Agent, or Firm* — Davis & Bujold PLLC; Charles G. Holoubek; Michael J. Bujold (57) ABSTRACT

A method of treating a disease condition in a mammal comprising administering a pharmacologically effective amount of a therapeutic, wherein the therapeutic includes a bioisosteres of caffeic acid. A pharmaceutical composition for treating a disease condition in a mammal comprising a first therapeutic that includes a bioisosteres of caffeic acid, wherein the condition may be breast cancer, and the pharmaceutical composition may include a second therapeutic for the disease condition that is not a bioisosteres of caffeic acid.

18 Claims, 7 Drawing Sheets

FIG. 1

CAPE (2)

Caffeic Acid (1)

CONFORMATIONALLY-CONSTRAINED BIOISOSTERES OF CAFFEIC ACID, AND SYNTHESIS AND THERAPEUTIC USES

CROSS REFERENCE TO RELATED APPLICATIONS/PRIORITY

The present invention claims priority to U.S. Provisional Patent Application Nos. 62/622,805 filed Jan. 26, 2018, 62/622,808 filed Jan. 26, 2018, 62/622,811 filed Jan. 26, 2018, 62/622,818 filed Jan. 26, 2018, 62/622,820 filed Jan. 26, 2018, and 62/622,822 filed Jan. 26, 2018, each of which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

BACKGROUND

Cancer and other conditions still plague our populations. For the foregoing reasons, there is a pressing, but seemingly irresolvable need for developing a treatment option and method to produce it.

SUMMARY

Wherefore, it is an object of the present invention to overcome the above mentioned shortcomings and drawbacks associated with the current technology. The present invention is directed to methods and apparatuses that satisfy the above shortcomings and drawbacks. The presently claimed invention relates to compositions and methods of treating a disease condition in a mammal comprising administering a pharmacologically effective amount of a therapeutic, wherein the therapeutic includes a bioisosteres of caffeic acid. According to a further embodiment the condition is a cancer. According to a further embodiment the condition is a breast cancer. According to a further embodiment the condition the therapeutic targets is one of MAP kinase ERK2, geminin, ATPase family AAA domain-containing protein 5, glucagon-like peptide 1 receptor, neuropeptide S receptor, chromobox protein homolog 1, DNA polymerase iota, beta, eta, and kappa, peptidyl-prolyl cis-trans isomerase NIMA-interacting 1, serine/threonine-protein kinase PLK1, endoplasmic reticulum-associated amyloid beta-peptide-binding protein, guanine nucleotide-binding protein G(s) subunit alpha, hypoxia-inducible factor 1 alpha, beta-lactamase AmpC, *E. coli* K-12, ATP-dependent molecular chaperone HSP82, candida Ras-related protein Rab-9A, Replicative DNA helicase, rattus tuberculosis premalin-A/C, albicans Huntington, microphthalmia-associated transcription factor, paired box protein Pax-8, DNA-(apurininc or apyrimidic site) lyase, Isocitrate dehydrogenase (NADP) cytoplasmic, microtubule-associated protein tau, histone-lysine N-methyltransferase (H3 lysine-9 specific 3), geminin, parathyroid hormone receptor, lysosomal alpha-glucosidase, Protein RecA, *Mycobacterium tuberculosis*, and *Trypanosoma brucei brucei*. According to a further embodiment the condition is a disease that is treated by targeting one of MAP kinase ERK2, geminin, ATPase family AAA domain-containing protein 5, glucagon-like peptide 1 receptor, neuropeptide S receptor, chromobox protein homolog 1, DNA polymerase iota, beta, eta, and kappa, peptidyl-prolyl cis-trans isomerase NIMA-interacting 1, serine/threonine-protein kinase PLK1, endoplasmic reticulum-associated amyloid beta-peptide-binding protein, guanine nucleotide-binding protein G(s) subunit alpha, hypoxia-inducible factor 1 alpha, beta-lactamase AmpC, *E. coli* K-12, ATP-dependent molecular chaperone HSP82, candida Ras-related protein Rab-9A, Replicative DNA helicase, rattus tuberculosis premalin-A/C, albicans Huntington, microphthalmia-associated transcription factor, paired box protein Pax-8, DNA-(apurininc or apyrimidic site) lyase, Isocitrate dehydrogenase (NADP) cytoplasmic, microtubule-associated protein tau, histone-lysine N-methyltransferase (H3 lysine-9 specific 3), geminin, parathyroid hormone receptor, lysosomal alpha-glucosidase, Protein RecA, *Mycobacterium tuberculosis*, and *Trypanosoma brucei brucei*. According to a further embodiment the mammal is human. According to a further embodiment the bioisosteres of caffeic acid is a conformationally-constrained bioisosteres of caffeic acid. According to a further embodiment the bioisoter of caffeic acid has one of the following chemical structures:

According to a further embodiment the bioisoter of caffeic acid has one of the following chemical structures:

where R is one of a alkyl group, an aryl group, an aryl/alkyl group, and an H.

The presently claimed invention further relates to methods and pharmaceutical compositions for treating a disease condition in a mammal comprising a first therapeutic that includes a bioisosteres of caffeic acid. According to a further embodiment the condition is a cancer. According to a further embodiment the condition is a breast cancer. According to a further embodiment, the pharmaceutical composition also includes a second therapeutic for the disease condition that is not a bioisosteres of caffeic acid. According to a further embodiment the bioisosteres of caffeic acid is a conformationally-constrained bioisosteres of caffeic acid. According to a further embodiment wherein the bioisoter of caffeic acid has one of the following chemical structures:

According to a further embodiment the bioisoter of caffeic acid has one of the following chemical structures:

where R is one of a alkyl group, an aryl group, an aryl/alkyl group, and an H.

The presently claimed invention further relates to chemicals comprising a bioisoters of caffeic acid having one of the following chemical structures:

where R is one of a alkyl group, an aryl group, an aryl/alkyl group, and an H. According to a further embodiment the bioisoteres has the chemical structure of one of the following:

The present invention relates to pharmaceutical compositions of a therapeutic (e.g., conformationally-constrained bioisoteres of caffeic acid), or a pharmaceutically acceptable salt, solvate, ester, amide, clathrate, stereoisomer, enantiomer, prodrug or analogs thereof, and use of these compositions for the treatment of a cancer, including human breast cancer.

In some embodiments, the therapeutic, or a pharmaceutically acceptable salt, solvate, or prodrug thereof, is administered as a pharmaceutical composition that further includes a pharmaceutically acceptable excipient.

In some embodiments, administration of the pharmaceutical composition to a human results in a peak plasma concentration of the therapeutic between 0.05 µM-10 µM (e.g., between 0.05 µM-5 µM).

In some embodiments, the peak plasma concentration of the therapeutic is maintained for up to 14 hours. In other embodiments, the peak plasma concentration of the therapeutic is maintained for up to 1 hour.

In some embodiments, the condition is a cancer.

In certain embodiments, the cancer is mild to moderate cancer.

In further embodiments, the cancer is moderate to severe cancer.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

In some embodiments, the pharmaceutical composition is administered concurrently with one or more additional therapeutic agents for the treatment or prevention of the cancer.

In some embodiments, the therapeutic, or a pharmaceutically acceptable salt, solvate, or prodrug thereof, is administered as a pharmaceutical composition that further includes a pharmaceutically acceptable excipient.

In some embodiments, administration of the pharmaceutical composition to a human results in a peak plasma concentration of the therapeutic between 0.05 µM-10 µM (e.g., between 0.05 µM-5 µM).

In some embodiments, the peak plasma concentration of the therapeutic is maintained for up to 14 hours. In other embodiments, the peak plasma concentration of the therapeutic is maintained for up to 1 hour.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

As used herein, the term "delayed release" includes a pharmaceutical preparation, e.g., an orally administered formulation, which passes through the stomach substantially intact and dissolves in the small and/or large intestine (e.g., the colon). In some embodiments, delayed release of the active agent (e.g., a therapeutic as described herein) results from the use of an enteric coating of an oral medication (e.g., an oral dosage form).

The term an "effective amount" of an agent, as used herein, is that amount sufficient to effect beneficial or desired results, such as clinical results, and, as such, an "effective amount" depends upon the context in which it is being applied.

The terms "extended release" or "sustained release" interchangeably include a drug formulation that provides for gradual release of a drug over an extended period of time, e.g., 6-12 hours or more, compared to an immediate release formulation of the same drug. Preferably, although not necessarily, results in substantially constant blood levels of a drug over an extended time period that are within therapeutic levels and fall within a peak plasma concentration range that is between, for example, 0.05-10 µM, 0.1-10 µM, 0.1-5.0 µM, or 0.1-1 µM.

As used herein, the terms "formulated for enteric release" and "enteric formulation" include pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®)), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

The term "immediate release" includes where the agent (e.g., therapeutic), as formulated in a unit dosage form, has a dissolution release profile under in vitro conditions in which at least 55%, 65%, 75%, 85%, or 95% of the agent is released within the first two hours of administration to, e.g., a human. Desirably, the agent formulated in a unit dosage has a dissolution release profile under in vitro conditions in which at least 50%, 65%, 75%, 85%, 90%, or 95% of the agent is released within the first 30 minutes, 45 minutes, or 60 minutes of administration.

The term "pharmaceutical composition," as used herein, includes a composition containing a compound described herein (e.g., conformationally-constrained bioisosteres, such as compound 6, compound 7, compound 8, compound 9, compounds 10, compounds 11 and compounds 12, or any pharmaceutically acceptable salt, solvate, or prodrug thereof), formulated with a pharmaceutically acceptable excipient, and typically manufactured or sold with the approval of a governmental regulatory agency as part of a therapeutic regimen for the treatment of disease in a mammal.

Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, includes any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, includes those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, includes those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate" or "solvate," as used herein, includes a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, includes prophylactic treatment or treatment that prevents one or more symptoms or conditions of a disease, disorder, or conditions described herein (e.g., a cancer). Treatment can be initiated, for example, prior to ("pre-exposure prophylaxis") or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, includes compounds which are rapidly transformed in vivo to the parent compound of the above formula. Prodrugs also encompass bioequivalent compounds that, when administered to a human, lead to the in vivo formation of therapeutic. Preferably, prodrugs of the compounds of the present invention are pharmaceutically acceptable.

As used herein, and as well understood in the art, "treatment" includes an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also include delaying the onset of, impeding or reversing the progress of, or alleviating either the disease or condition to which the term applies, or one or more symptoms of such disease or condition.

The term "unit dosage forms" includes physically discrete units suitable as unitary dosages for human subjects and other mammals, each unit containing a predetermined quantity of active material calculated to produce the desired therapeutic effect, in association with any suitable pharmaceutical excipient or excipients.

As used herein, the term "plasma concentration" includes the amount of therapeutic present in the plasma of a treated subject (e.g., as measured in a rabbit using an assay described below or in a human).

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which.

DETAILED DESCRIPTION

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1-7, a brief description concerning the various components of the present invention will now be briefly discussed.

Novel bioisosteric analogs of caffeic acid have been designed and the synthesis of tetrazole compound 7 has been achieved in five steps from commercially available aldehyde compound 3. Compound 7 displays significant anti-proliferative activity against triple negative breast cancer cells in cell proliferation studies, which is greater than caffeic acid itself. Based on this proof-of-concept study with compound 7 as an anti-cancer agent, other novel caffeic acid analogs are proposed.

The inventors are aware of various polyphenol compounds derived from fruits and vegetables have been shown to induce apoptotic pathways and to suppress cancer cell proliferation. Caffeic acid (3,4-dihydroxy cinnamic acid, compound 1) is a simple polyphenolic compound found primarily in coffee. Studies have shown that it has anti-oxidative, anti-inflammatory, and anti-cancer activity. It also manifests its anti-cancer activity through increased levels of reactive oxygen species (ROS and altered mitochondrial membrane potential.

Certain derivatives of caffeic acid display even greater anti-cancer activity and other beneficial medicinal properties.

For example, caffeic acid phenethyl ester (CAPE, 2), a natural product derived from honeybee hive propolis, has been shown to have anti-mitogenic, anti-cancer, and anti-allergenic effects. Many of these effects are mediated through its inhibition of NF-κB signaling and of various signaling pathways in cancer cells.

The inventor see great promise in the development of novel synthetic analogs of caffeic acid with cancer chemopreventive and chemotherapeutic potential by targeting cell signaling pathways, mitochondrial properties, inflammation, and phenotypic morphology of cancer cells.

Figure 1:
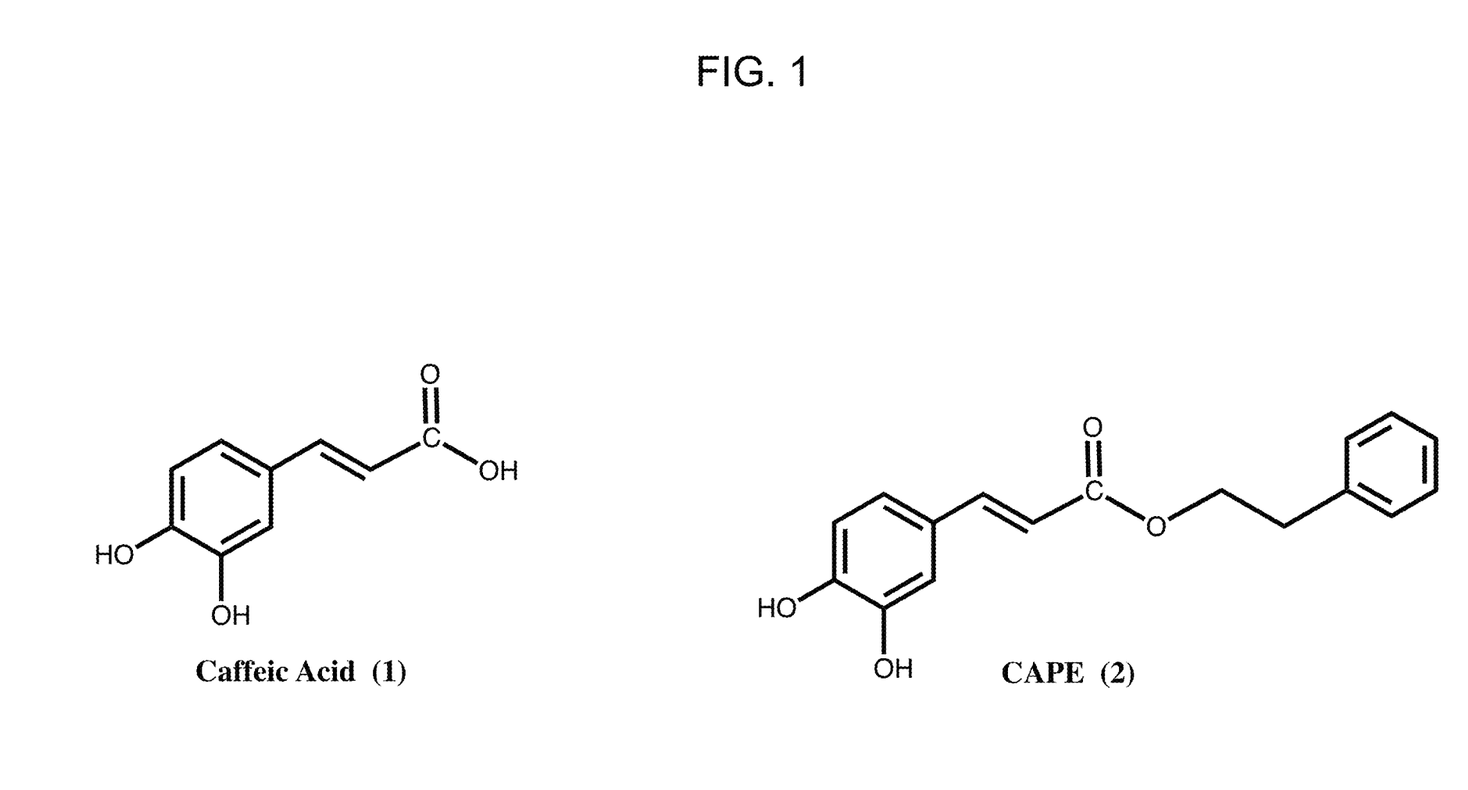
FIG. 1 shows the chemical structures of Caffeic acid (1) and CAPE (2).
Figure 2:
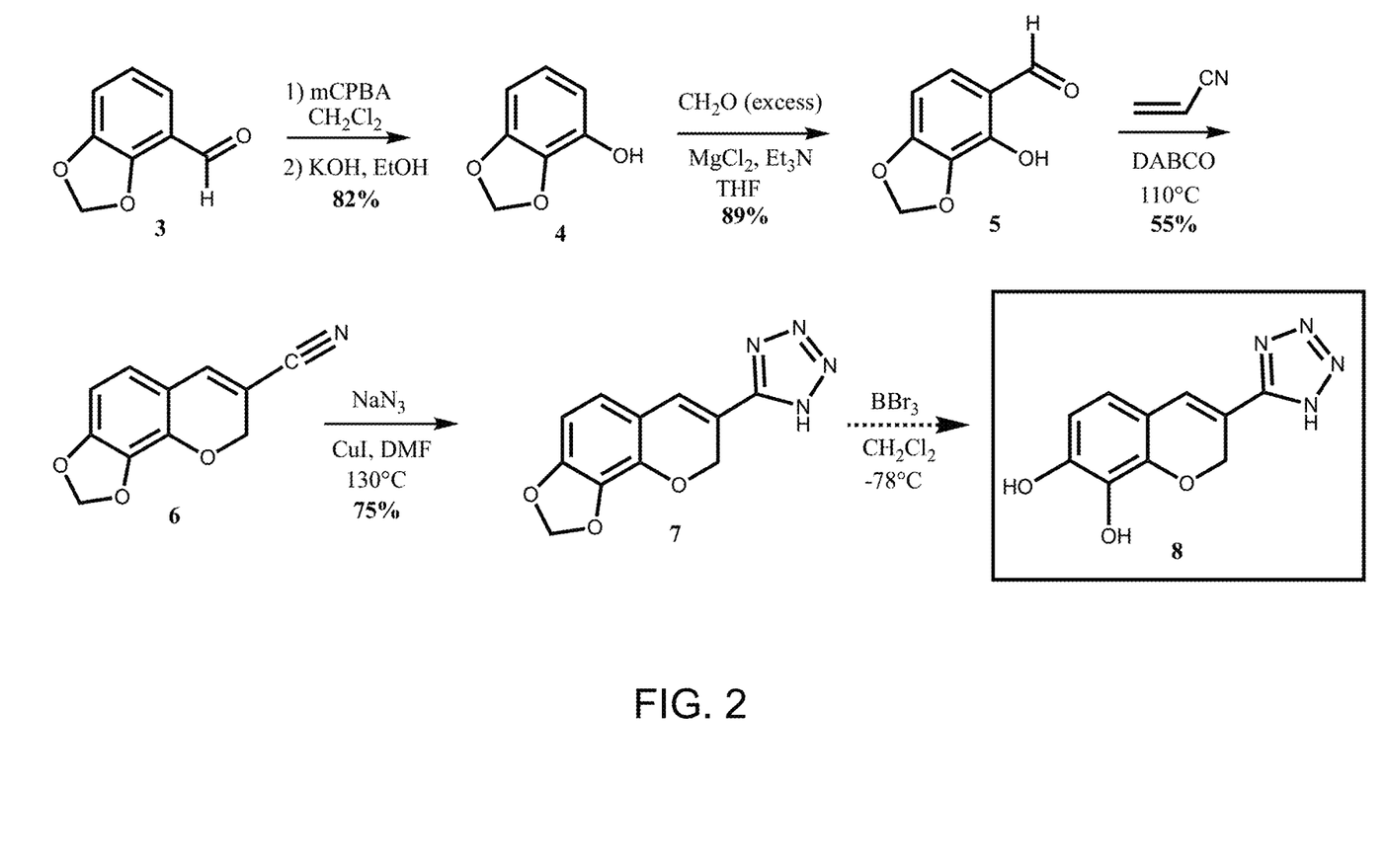
FIG. 2 shows a method for the synthesis of conformationally-constrained caffeic acid tetrazole bioisostere (8).
Figure 3:
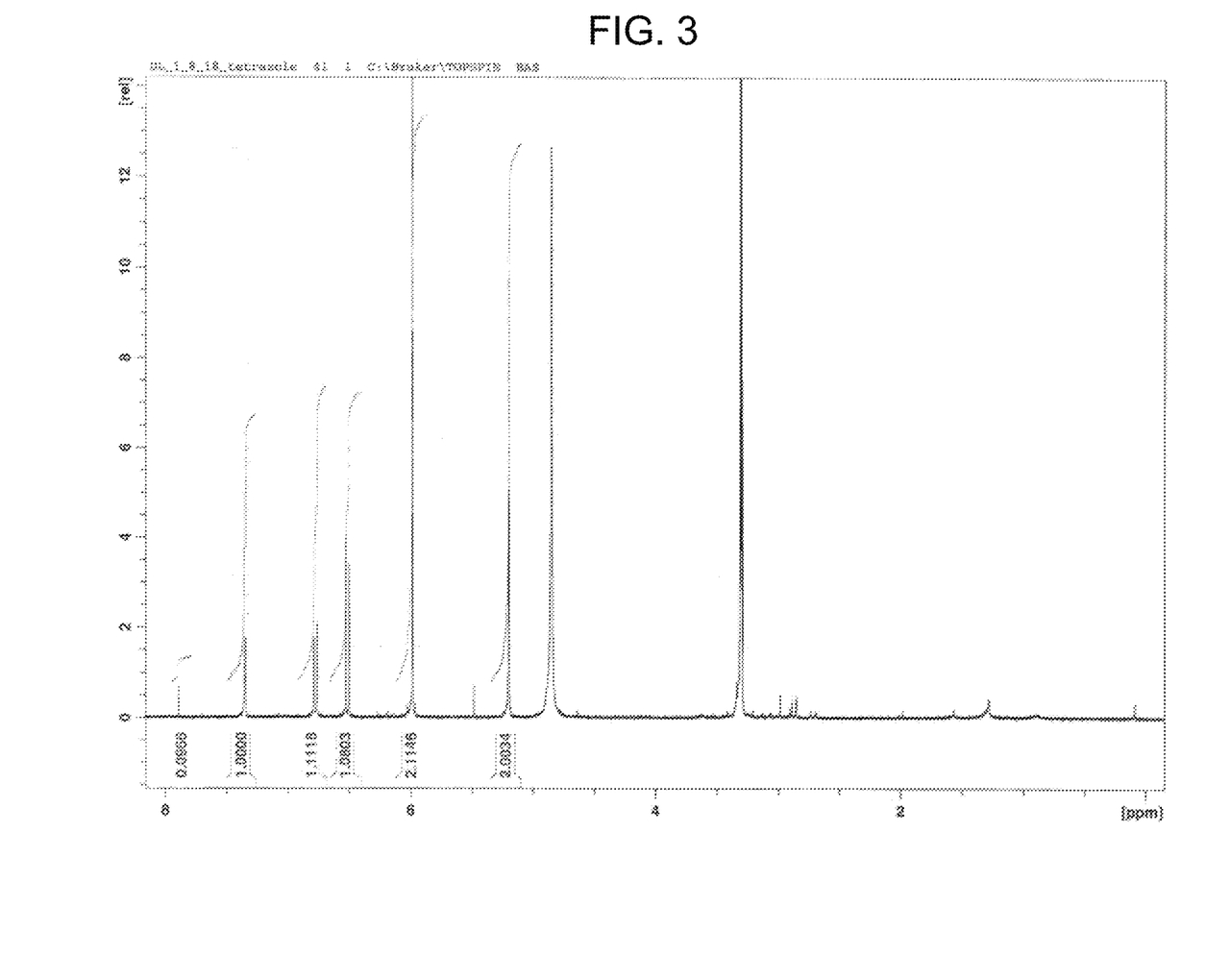
FIG. 3 is a 300 MHz $^1$H $^{13}$C NMR spectra of protected tetrazole acetal (7).
Figure 4:
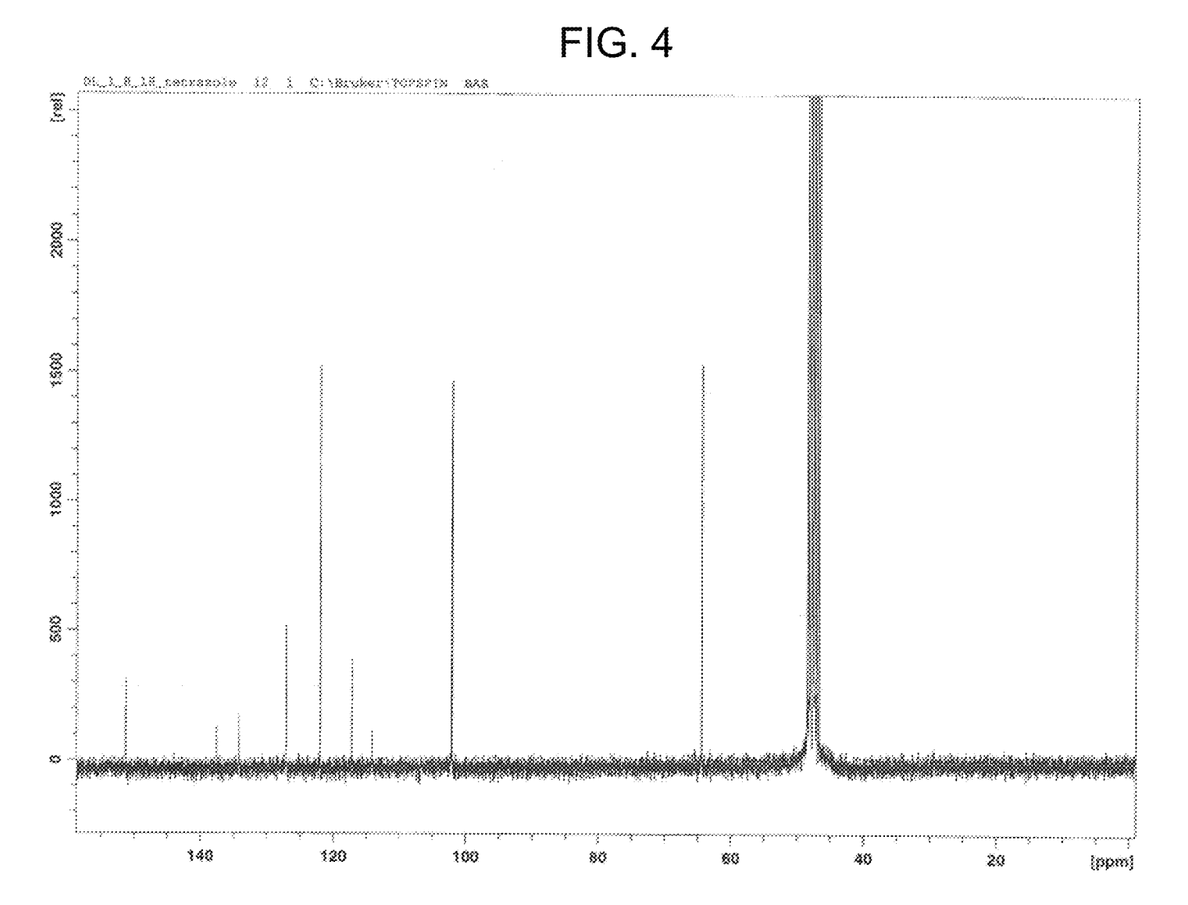
FIG. 4 is 75 MHz $^{13}$C NMR spectra of protected tetrazole acetal (7).

The inventor prepared tetrazole acetyl booster (compound 7) through a 5-step synthesis, starting with commercially available diesoline aldehyde (compound 3). Baeyer-Villiger oxidation and hydrolysis of the incipient ester provides phenol (compound 4). Electrophilic substitution ortho to the phenol, accompanied by concurrent oxidation with excess paraformaldehyde to give aldehyde (compound 5). Note that compound 4 and compound 5 are a known compound. Cyclization is achieved by heating compound 5 with acrylonitrile in 1,4-Diazabicyclo[2.2.2]octane (DABCO) to give the novel benzopyran nitrile (compound 6). Treatment of compound 6 with sodium azide in DMF and a small catalytic amount (0.5-1.0 mol %) of copper (I) iodide furnished the tetrazole acetal (compound 7). The catechol hydroxyl groups will be deprotected as illustrated ($BBr_3$ in $CH_2Cl_2$ at −78° C.) to furnish target compound (compound 8).

Figure 5:
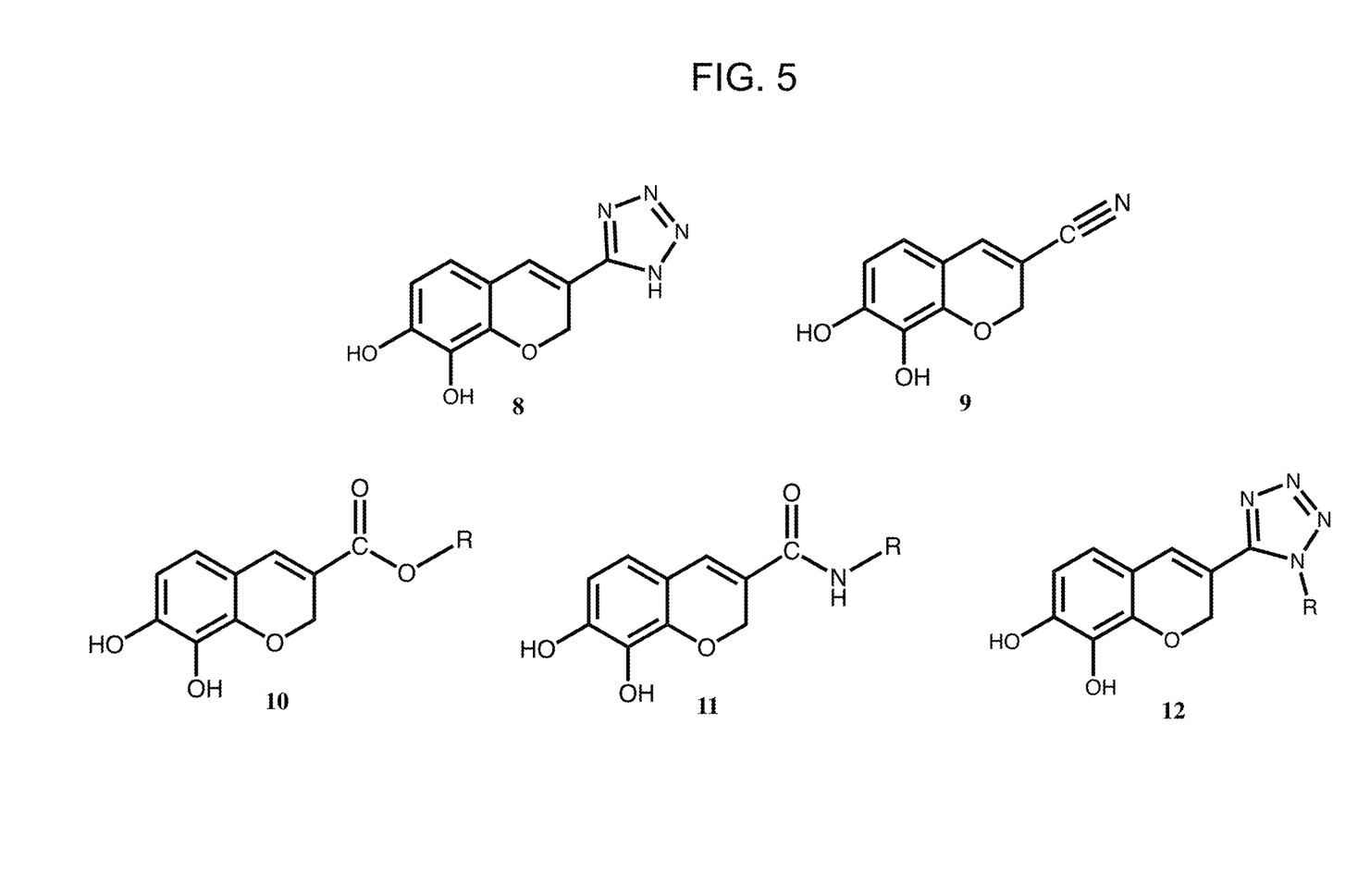
FIG. 5 shows the chemical structures of Novel Conformationally Constrained Caffeic Acid Derivatives, where R=alkyl, aryl, and aryl/alkyl (e.g. phenethyl, alkyl imidazole, alkyl oxazole, etc).
Figure 6:
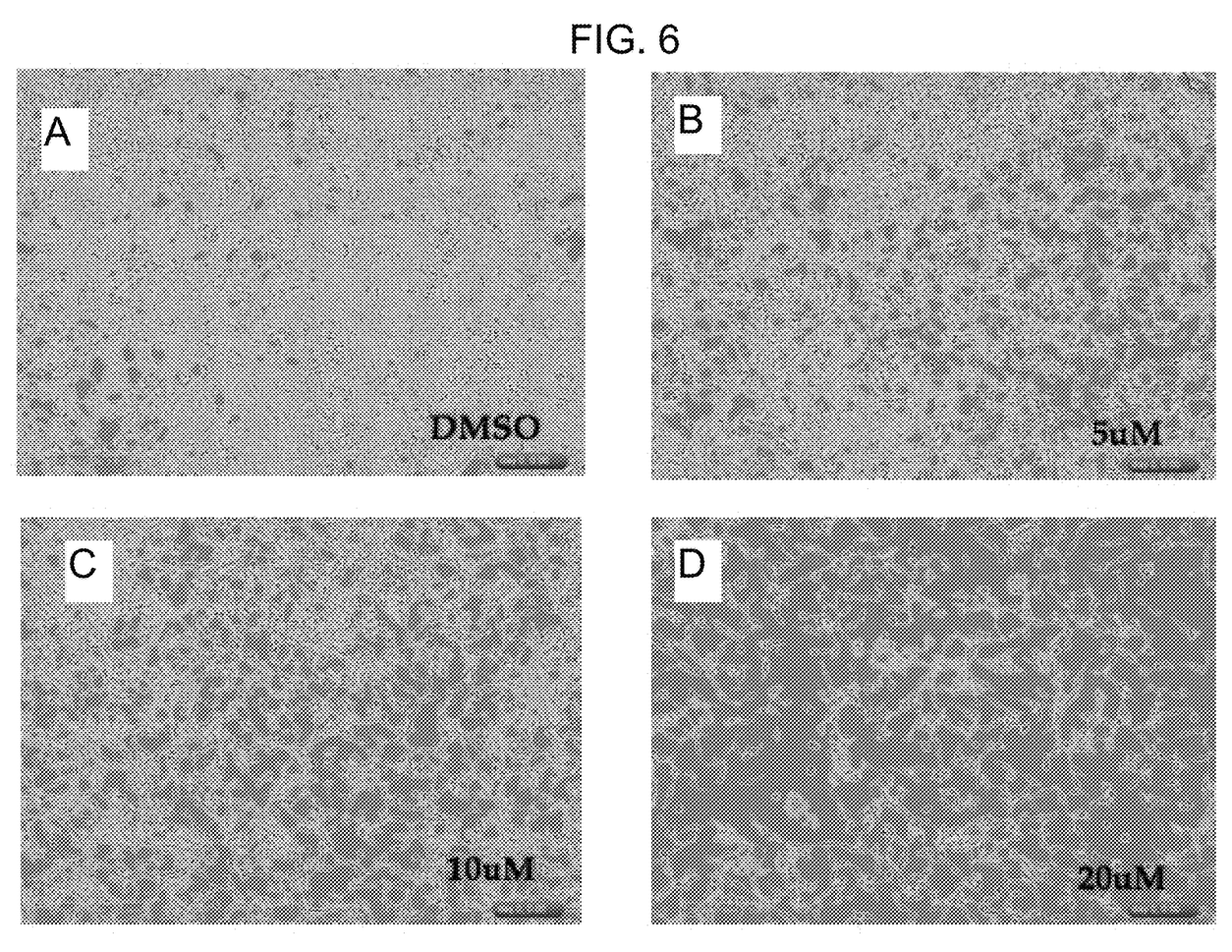
FIG. 6 shows IncuCyte high definition phase contrast imaging of Triple Negative Breast Cancer MDA-MB-231 cell line treated with DMSO control (box A) and compound 7 at concentrations of 5 uM (box B), 10 uM (box C), and 20 uM (box D). The images were taken after 72 hours. In these images, the yellow color (or lighter color in the black and white versions) denotes the cancer cells and the grey color (or darker color in the black and white versions) represents the media.
Figure 7:
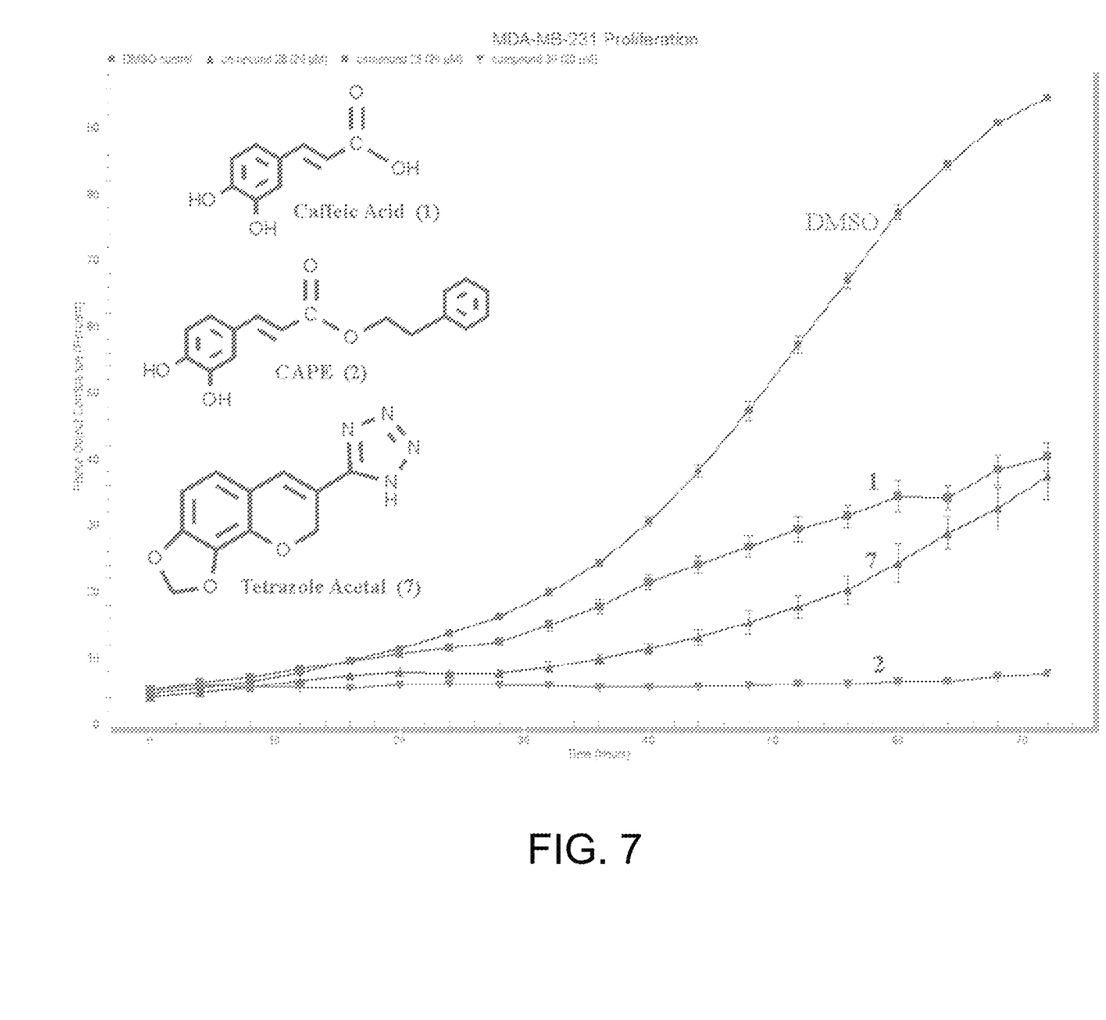
FIG. 7 shows IncuCyte Cell Proliferation Assay with Triple Negative Breast Cancer (72 hrs.): DMSO control; caffeic acid (compound 1); protected tetrazole (compound 7) and CAPE (compound 2).

Turning to FIG. 5, based on the inventor's assay results and characteristics know to the inventor of the caffeic acid acetal vs. caffeic acid (1) against triple negative breast cancer, the inventor hypothesized that deprotected compound 8 should show significantly more anti-proliferative anti-cancer activity than tetrazole acetal (compound 7), which itself shows anti-proliferative anti-cancer activity.

Putative drug candidates disclosed herein also embodies molecules in which the catechol groups are alkylated (as ethers) or are protected as alkyl ketals or acetals (analogous to compound 7).

CSNAP (Chemical Similarity Search Array Pulldown) search: A chemical similarity search conducted with the 3D version of the analysis software CSNAP showed that the proposed drug candidates represented in FIG. 5 were deemed to be chemically similar with known drugs possessing the following known pharmaceutical targets. The inventor therefore anticipates that the caffeic acid analogs proposed herein may have utility in affecting the following drug targets.

MAP kinase ERK2, geminin, ATPase family AAA domain-containing protein 5, glucagon-like peptide 1 receptor, neuropeptide S receptor, chromobox protein homolog 1, DNA polymerase iota, beta, eta, and kappa, peptidyl-prolyl cis-trans isomerase NIMA-interacting 1, serine/threonine-protein kinase PLK1, endoplasmic reticulum-associated amyloid beta-peptide-binding protein, guanine nucleotide-binding protein G(s) subunit alpha, hypoxia-inducible factor 1 alpha, beta-lactamase AmpC, *E. coli* K-12, ATP-dependent molecular chaperone HSP82, candida Ras-related protein Rab-9A, Replicative DNA helicase, rattus tuberculosis pre-malin-A/C, albicans Huntington, microphthalmia-associated transcription factor, paired box protein Pax-8, DNA-(apurinic or apyrimidic site) lyase, Isocitrate dehydrogenase (NADP) cytoplasmic, microtubule-associated protein tau, histone-lysine N-methyltransferase (H3 lysine-9 specific 3), geminin, parathyroid hormone receptor, lysosomal alpha-glucosidase, Protein RecA, *Mycobacterium tuberculosis*, and *Trypanosoma brucei brucei*.

Pharmaceutical Compositions

The methods described herein can also include the administrations of pharmaceutically acceptable compositions that include the therapeutic, or a pharmaceutically acceptable salt, solvate, or prodrug thereof. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention can be administered alone, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are described in *Remington: The Science and Practice of Pharmacy,* $22^{nd}$ Ed., Gennaro, Ed., Lippencott Williams & Wilkins (2012), a well-known reference text in this field, and in the USP/NF (United States Pharmacopeia and the National Formulary), each of which is incorporated by reference. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The methods described herein can include the administration of a therapeutic, or prodrugs or pharmaceutical compositions thereof, or other therapeutic agents.

The pharmaceutical compositions can be formulated so as to provide immediate, extended, or delayed release of the active ingredient after administration to the patient by employing procedures known in the art.

The compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or, from about 100 mg to about 250 mg of the active ingredient. For preparing solid compositions such as tablets, the principal active ingredient is mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions suitable for oral mucosal administration (e.g., buccal or sublingual administration) include tablets, lozenges, and pastilles, where the active ingredient is formulated with a carrier, such as sugar, acacia, tragacanth, or gelatin and glycerine.

Coatings

The pharmaceutical compositions formulated for oral delivery, such as tablets or capsules of the present invention can be coated or otherwise compounded to provide a dosage form affording the advantage of delayed or extended release. The coating may be adapted to release the active drug substance in a predetermined pattern (e.g., in order to achieve a controlled release formulation) or it may be adapted not to release the active drug substance until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succiante, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the drug is released in the lower gastrointestinal tract.

In addition to coatings that effect delayed or extended release, the solid tablet compositions may include a coating adapted to protect the composition from unwanted chemical changes (e.g., chemical degradation prior to the release of the active drug substance).

Parenteral Administration

Within the scope of the present invention are also parenteral depot systems from biodegradable polymers. These systems are injected or implanted into the muscle or subcutaneous tissue and release the incorporated drug over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 µm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Mucosal Drug Delivery

Mucosal drug delivery (e.g., drug delivery via the mucosal linings of the nasal, rectal, vaginal, ocular, or oral cavities) can also be used in the methods described herein. Methods for oral mucosal drug delivery include sublingual administration (via mucosal membranes lining the floor of the mouth), buccal administration (via mucosal membranes lining the cheeks), and local delivery (Harris et al., *Journal of Pharmaceutical Sciences,* 81(1): 1-10, 1992).

Oral transmucosal absorption is generally rapid because of the rich vascular supply to the mucosa and allows for a rapid rise in blood concentrations of the therapeutic.

For buccal administration, the compositions may take the form of, e.g., tablets, lozenges, etc. formulated in a conventional manner. Permeation enhancers can also be used in buccal drug delivery. Exemplary enhancers include 23-lauryl ether, aprotinin, azone, benzalkonium chloride, cetylpyridinium chloride, cetyltrimethylammonium bromide, cyclodextrin, dextran sulfate, lauric acid, lysophosphatidylcholine, methol, methoxysalicylate, methyloleate, oleic acid, phosphatidylcholine, polyoxyethylene, polysorbate 80, sodium EDTA, sodium glycholate, sodium glycodeoxycholate, sodium lauryl sulfate, sodium salicylate, sodium taurocholate, sodium taurodeoxycholate, sulfoxides, and alkyl glycosides. Bioadhesive polymers have extensively been employed in buccal drug delivery systems and include cyanoacrylate, polyacrylic acid, hydroxypropyl methylcellulose, and poly methacrylate polymers, as well as hyaluronic acid and chitosan.

Liquid drug formulations (e.g., suitable for use with nebulizers and liquid spray devices and electrohydrodynamic (EHD) aerosol devices) can also be used. Other methods of formulating liquid drug solutions or suspension suitable for use in aerosol devices are known to those of skill in the art.

Formulations for sublingual administration can also be used, including powders and aerosol formulations. Exemplary formulations include rapidly disintegrating tablets and liquid-filled soft gelatin capsules.

Dosing Regimes

The present methods for treating cancers are carried out by administering a therapeutic for a time and in an amount sufficient to result in decreased tumor growth, decreased tumor size, or decreased tumor number, for example.

The amount and frequency of administration of the compositions can vary depending on, for example, what is being administered, the state of the patient, and the manner of administration. In therapeutic applications, compositions can be administered to a patient suffering from cancer in an amount sufficient to relieve or least partially relieve the symptoms of the cancer and its complications. The dosage is likely to depend on such variables as the type and extent of progression of the cancer, the severity of the cancer, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of the cancer or slowing its progression.

The amount of therapeutic per dose can vary. For example, a subject can receive from about 0.1 µg/kg to about 10,000 µg/kg. Generally, the therapeutic is administered in an amount such that the peak plasma concentration ranges from 150 nM-250 µM.

Exemplary dosage amounts can fall between 0.1-5000 µg/kg, 100-1500 µg/kg, 100-350 µg/kg, 340-750 µg/kg, or 750-1000 µg/kg. Exemplary dosages can 0.25, 0.5, 0.75, 1°, or 2 mg/kg. In another embodiment, the administered dosage can range from 0.05-5 mmol of therapeutic (e.g., 0.089-3.9 mmol) or 0.1-50 µmol of therapeutic (e.g., 0.1-25 µmol or 0.4-20 µmol).

The plasma concentration of therapeutic can also be measured according to methods known in the art. Exemplary peak plasma concentrations of therapeutic can range from 0.05-10 µM, 0.1-10 µM, 0.1-5.0 µM, or 0.1-1 µM. Alternatively, the average plasma levels of therapeutic can range from 400-1200 µM (e.g., between 500-1000 µM) or between 50-250 µM (e.g., between 40-200 µM). In some embodiments where sustained release of the drug is desirable, the peak plasma concentrations (e.g., of therapeutic) may be maintained for 6-14 hours, e.g., for 6-12 or 6-10 hours. In other embodiments where immediate release of the drug is desirable, the peak plasma concentration (e.g., of therapeutic) may be maintained for, e.g., 30 minutes.

The frequency of treatment may also vary. The subject can be treated one or more times per day with therapeutic (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Kits

Any of the pharmaceutical compositions of the invention described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention to reduce symptoms and/or underlying cause of the cancer.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

I claim:

1. A method of treating breast cancer in a mammal comprising:
    administering a pharmacologically effective amount of a therapeutic;
    wherein the therapeutic includes a bioisostere of caffeic acid;
    and the bioisostere of caffeic acid has one of the following chemical structures, where R is one of an alkyl group, an aryl group, an aryl/alkyl group, and a H:

-continued or a salt, solvate, ester, amide, clathrate, stereoisomer, enantiomer, prodrug or analog thereof.

2. The method of claim 1 wherein the mammal is human.

3. A chemical comprising:
a bioisoter of caffeic acid having one of the following chemical structures where R is one of an alkyl group, an aryl group, an aryl/alkyl group, and a H:

-continued or a salt, solvate, ester, amide, clathrate, stereoisomer, enantiomer, prodrug or analog thereof.

4. The chemical of claim 3 wherein the bioisotere has the chemical structure of one of the following:

21
-continued and or a salt, solvate, ester, amide, clathrate, stereoisomer, enantiomer, prodrug or analog thereof.

5. The method of claim 1 wherein the bioisostere of caffeic acid has the following chemical structure:

or a salt, solvate, ester, amide, clathrate, stereoisomer, enantiomer, prodrug or analog thereof.

6. The method of claim 1 wherein the bioisostere of caffeic acid has the following chemical structure:

or a salt, solvate, ester, amide, clathrate, stereoisomer, enantiomer, prodrug or analog thereof.

7. The method of claim 1 wherein the bioisostere of caffeic acid has the following chemical structure:

22 or a salt, solvate, ester, amide, clathrate, stereoisomer, enantiomer, prodrug or analog thereof.

8. The method of claim 1 wherein the bioisostere of caffeic acid has the following chemical structure:

or a salt, solvate, ester, amide, clathrate, stereoisomer, enantiomer, prodrug or analog thereof.

9. The method of claim 1 wherein the bioisostere of caffeic acid has the following chemical structure, where R is one of an alkyl group, an aryl group, an aryl/alkyl group, and a H:

or a salt, solvate, ester, amide, clathrate, stereoisomer, enantiomer, prodrug or analog thereof.

10. The method of claim 1 wherein the bioisostere of caffeic acid has the following chemical structure, where R is one of an alkyl group, an aryl group, an aryl/alkyl group, and a H:

or a salt, solvate, ester, amide, clathrate, stereoisomer, enantiomer, prodrug or analog thereof.

11. The method of claim 1 wherein the bioisostere of caffeic acid has the following chemical structure, where R is one of an alkyl group, an aryl group, an aryl/alkyl group, and a H:

or a salt, solvate, ester, amide, clathrate, stereoisomer, enantiomer, prodrug or analog thereof.

12. The chemical of claim 3 wherein the bioisotere has the chemical structure of:

or a salt, solvate, ester, amide, clathrate, stereoisomer, enantiomer, prodrug or analog thereof.

13. The chemical of claim 3 wherein the bioisotere has the chemical structure of:

or a salt, solvate, ester, amide, clathrate, stereoisomer, enantiomer, prodrug or analog thereof.

14. The chemical of claim 3 wherein the bioisotere has the chemical structure of:

or a salt, solvate, ester, amide, clathrate, stereoisomer, enantiomer, prodrug or analog thereof.

15. The chemical of claim 3 wherein the bioisotere has the chemical structure of:

or a salt, solvate, ester, amide, clathrate, stereoisomer, enantiomer, prodrug or analog thereof.

16. The chemical of claim 3 wherein the bioisostere of caffeic acid has the following chemical structure, where R is one of an alkyl group, an aryl group, an aryl/alkyl group, and a H:

or a salt, solvate, ester, amide, clathrate, stereoisomer, enantiomer, prodrug or analog thereof.

17. The chemical of claim 3 wherein the bioisostere of caffeic acid has the following chemical structure, where R is one of an alkyl group, an aryl group, an aryl/alkyl group, and a H:

or a salt, solvate, ester, amide, clathrate, stereoisomer, enantiomer, prodrug or analog thereof.

18. Chemical of claim 3 wherein the bioisostere of caffeic acid has the following chemical structure, where R is one of an alkyl group, an aryl group, an aryl/alkyl group, and a H:

or a salt, solvate, ester, amide, clathrate, stereoisomer, enantiomer, prodrug or analog thereof.

* * * * *